US009801825B2

(12) United States Patent
Marius et al.

(10) Patent No.: US 9,801,825 B2
(45) Date of Patent: *Oct. 31, 2017

(54) CARBOHYDRATE TABLET AND METHOD OF FABRICATION

(71) Applicants: Frederick S. Marius, Winchester, MA (US); Richard Marius, Nashville, TN (US)

(72) Inventors: Frederick S. Marius, Winchester, MA (US); Richard Marius, Nashville, TN (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/661,908

(22) Filed: Mar. 18, 2015

(65) Prior Publication Data

US 2016/0271068 A1    Sep. 22, 2016

(51) Int. Cl.
| | |
|---|---|
| *A61K 9/20* | (2006.01) |
| *A23P 10/28* | (2016.01) |
| *A23L 29/30* | (2016.01) |
| *A23P 10/25* | (2016.01) |
| *A23L 33/10* | (2016.01) |
| *A23L 33/115* | (2016.01) |
| *A23L 33/15* | (2016.01) |
| *A23L 33/175* | (2016.01) |
| *A61K 9/00* | (2006.01) |
| *A61J 3/10* | (2006.01) |

(52) U.S. Cl.
CPC ............ *A61K 9/2095* (2013.01); *A23L 29/30* (2016.08); *A23L 29/35* (2016.08); *A23L 33/10* (2016.08); *A23L 33/115* (2016.08); *A23L 33/15* (2016.08); *A23L 33/175* (2016.08); *A23P 10/25* (2016.08); *A23P 10/28* (2016.08); *A61J 3/10* (2013.01); *A61K 9/0056* (2013.01); *A61K 9/2013* (2013.01); *A61K 9/2018* (2013.01); *A61K 9/2059* (2013.01)

(58) Field of Classification Search
CPC ... A61K 9/1682; A61K 9/1688; A61K 9/1694
See application file for complete search history.

(56) References Cited

U.S. PATENT DOCUMENTS

| | | | |
|---|---|---|---|
| 5,609,883 A * | 3/1997 | Valentine | A61K 9/2095 424/464 |
| 6,039,813 A | 3/2000 | Pepper et al. | |
| 6,277,407 B1 * | 8/2001 | Marius | B30B 15/0082 424/464 |
| 8,937,049 B2 | 1/2015 | Stellingwerff et al. | |
| 2006/0280777 A1 | 12/2006 | Schydlowsky | |
| 2007/0237855 A1 * | 10/2007 | Tancredi | A23G 3/36 426/3 |
| 2009/0226542 A1 | 9/2009 | Cresta | |
| 2011/0071185 A1 | 3/2011 | Bunick et al. | |

OTHER PUBLICATIONS

"Guenergy Co.", www.guenergy.co.uk; downloaded on Mar. 16, 2015 fromwebsite http:www.guenergy.co.uk/products/gu-energy-gel/ingredients-benefits_learn-the Science.; 1/3 pages.

* cited by examiner

*Primary Examiner* — Micah Paul Young
(74) *Attorney, Agent, or Firm* — Davis, Malm & D'Agostine, P.C.

(57) ABSTRACT

An edible energy tablet containing at least 80 weight % carbohydrates for consumption during exercise, is fabricated by a process including providing tablet material free of hydrophobic and/or PEG lubricants and free of $CO_2$ sources. The tablet material includes a sucrose and dextrose mixture of 77-95 wt. %, maltodextrin of 2-13 wt. %, an edible soluble oil of 0.2-2.0 wt. %, and an edible acid of 1-4 wt. %. The tablet material is introduced to a tablet press that alternately moves first and second punches towards and away from one another to compress the tablet material to form and release a tablet. A punch cleaner engaged with the first and second punches removes tablet material from the punches after tablet release. The tablet has a diameter of 1.2 to 3.8 cm, a thickness of 0.6 cm to 2.3 cm, and a resistance to breakage forces of 8.5 to 30 kilopounds.

52 Claims, 4 Drawing Sheets

CARBOHYDRATE TABLET AND METHOD OF FABRICATION

BACKGROUND OF THE INVENTION

1. Field of the Invention

This invention relates to sports nutrition. In particular, the present invention relates to the formulation and fabrication of a novel carbohydrate tablet for use by endurance athletes during training and competition.

2. Background Information

Sport drinks, bars, gels and chews are commonly used by athletes during long distance training and competitions such as marathons and triathlons, to try to replenish nutrients that are depleted by physical exertion. While many of these products help achieve their intended goals, many of them have drawbacks, such as being difficult to consume during training and competition and/or a tendency to cause gastrointestinal distress or stomach discomfort when consumed during training or competition at recommended levels. Manufacturing limitations have also restricted the types of available products.

A need exists for an improved product capable of providing nutrition to athletes during training and competition, and a method for packaging and fabricating the same.

SUMMARY

According to an embodiment of this invention, an edible energy tablet containing at least 80 weight % carbohydrates for consumption during exercise, is fabricated by a process that includes providing tablet material being free of hydrophobic and/or PEG lubricants and being free of $CO_2$ sources. The tablet material includes a sucrose and dextrose mixture of 77-95 wt. %, maltodextrin of 2-13 wt. %, an edible soluble oil of 0.2-2.0 wt. %, an edible acid of 1-4 wt. %, and flavor 0.5-3 wt. %. The process also includes providing a tablet press including at least one die circuitously moveable about the press and adapted for receiving tablet material therein; and a first punch and a second punch, the first and second punches being circuitously moveable with, and being adapted for operative engagement with, the die. A punch movement device is adapted to alternately move at least one of the first and second punches relatively towards and away from an other of the first and second punches to alternately compress the tablet material in the at least one die to form the tablet, and release the tablet. A punch cleaner is disposed in operative engagement with the first and second punches, the punch cleaner being adapted to remove tablet material from the first and second punches after each of the first and second punches has released the tablet.

The process also includes introducing the tablet material in the form of powder or granules to the die; moving the punches towards one another to compress the tablet material to form the tablet; moving the punches away from one another to release the tablet; and engaging the punch cleaner with each of the working faces to remove tablet material therefrom; wherein the tablet has a diameter in a range of about 0.5 to 1.5 inches (1.2 to 3.8 cm), a thickness within a range of about 0.25 inch to 0.9 inch (0.6 cm to 2.3 cm), and a resistance to breakage forces within a range of from 8.5 to 30 kilopounds; and the tablet material has a grit size in a range of about 930 to 3460 microns.

The present invention provides, in another aspect, a method for fabricating an edible energy tablet containing at least 80 weight % carbohydrates for consumption during exercise, is fabricated by a process that includes providing tablet material being free of hydrophobic and/or PEG lubricants and being free of $CO_2$ sources. The tablet material includes a sucrose and dextrose mixture of 77-95 wt. %, maltodextrin of 2-13 wt. %, an edible soluble oil of 0.2-2.0 wt. %, an edible acid of 1-4 wt. %, and flavor 0.5-3 wt. %. The method also includes providing a tablet press including at least one die circuitously moveable about the press and adapted for receiving tablet material therein; and a first punch and a second punch, the first and second punches being circuitously moveable with, and being adapted for operative engagement with, the die. A punch movement device is adapted to alternately move at least one of the first and second punches relatively towards and away from an other of the first and second punches to alternately compress the tablet material in the at least one die to form the tablet, and release the tablet. A punch cleaner is disposed in operative engagement with the first and second punches, the punch cleaner being adapted to remove tablet material from the first and second punches after each of the first and second punches has released the tablet.

The method further includes introducing the tablet material in the form of powder or granules to the die; moving the punches towards one another to compress the tablet material to form the tablet; moving the punches away from one another to release the tablet; and engaging the punch cleaner with each of the working faces to remove tablet material therefrom; wherein the tablet has a diameter in a range of about 0.5 to 1.5 inches (1.2 to 3.8 cm), a thickness within a range of about 0.25 inch to 0.9 inch (0.6 cm to 2.3 cm), and a resistance to breakage forces within a range of from 8.5 to 30 kilopounds; and the tablet material has a grit size in a range of about 930 to 3460 microns.

The above and other features and advantages of this invention will be more readily apparent from a reading of the following detailed description of various aspects of the invention taken in conjunction with the accompanying drawings.

DETAILED DESCRIPTION OF THE PREFERRED EMBODIMENTS

Referring to the figures set forth in the accompanying Drawings, the illustrative embodiments of the present invention will be described in detail hereinbelow. For clarity of exposition, like features shown in the accompanying Drawings are indicated with like reference numerals and similar features as shown in alternate embodiments in the Drawings are indicated with similar reference numerals.

Decades of scientific research have shown that consuming carbohydrates during exercise lasting longer than 2 hours helps to prevent/attenuate the dreaded 'honk' caused by muscle glycogen depletion. It has also been understood that endurance exercise, and in particular running, has been associated with gastro-intestinal (GI) disturbances which can ultimately affect performance. Upper GI symptoms include reflux, nausea, bloating, and upper abdominal cramping. Many of these symptoms have been shown to be exacerbated with fluid intake, and specifically carbohydrate intake, which slows gastric emptying and can lead to significant GI disturbances.

Having competed in long distance IRONMAN® (World Triathlon Corporation, Tampa Fla.) triathlons over the course of two decades, the instant inventor has been struck with the fact that despite the long understood need, an optimal solution for replenishing nutrients expended by long distance athletes has not been developed. Instead, a great deal of disparate and seemingly contradictory information has been promulgated. The present inventor recognized, for example, that while some approaches focus on simply providing carbohydrates, other approaches combine carbohydrates with protein in sport drinks, and combine carbohydrates with protein, fat, fillers, and/or various micronutrients in the form of sport bars and the like. Still other approaches parse the particular type of carbohydrates, recommending, for example, a single simple carbohydrate, while others recommend a combination of carbohydrates which may include complex carbohydrates. In addition, some approaches favor liquids (sport drinks), while others favor solids (sport bars) and hybrids (gels and/or chews). The present inventor has challenged this often contradictory conventional wisdom while recognizing and overcoming various drawbacks associated with them, to produce the present invention.

The instant inventor has recognized, for example, that although they hydrate and provide energy, sport drinks would need to be consumed in particularly large volumes to deliver the amount of carbohydrates ideally needed for long duration events (2+ hours). The human body can absorb between 60-90 grams of carbohydrates per hour during exercise. An athlete would need to consume 32-50 ounces of a typical sport drink each hour in order to reach 60-90 grams. The inventor has recognized that this level of consumption would be difficult, if not impossible to achieve in most instances, and even if possible, would very likely cause the aforementioned gastro-intestinal distress.

The inventor has also recognized that a combination of multiple carbohydrate sources has reportedly provided a higher level of carbohydrate delivery during exercise than a single carbohydrate source. Again, however, this effect was observed when the carbohydrates were consumed in sport drinks in large volumes, thereby implicating the same GI distress.

It has also generally been understood that protein, fat and fillers are needed along with carbohydrates, in order to provide a solid food product, such as sport bars. The present inventor has recognized that while sport bars provide the athlete with an alternative to sport drinks, they are in many respects poorly suited to long distance competitions. Although portable, they tend not to handle temperature extremes well (they freeze during winter sports and become sticky during summer months). Due to their texture and chewiness, they can be difficult to consume during intense activity. And, the added ingredients, including protein, and fillers, etc., tend to slow down absorption, leading to the feeling of being 'heavy on the stomach'.

Energy gels deliver a very concentrated amount of energy typically in the form of complex carbohydrates (e.g., 70-80% maltodextrin) that tends to be lighter on the stomach than energy bars, less susceptible to temperature fluctuations (they tend not to freeze or melt) and due to their flexible small size, they fit into small pockets. The predominance of maltodextrin is also taught to be more quickly digested than many simple carbohydrates, without producing "a sugar high like you experience with simple sugars." (See, e.g., http://www.guenergy.co.uk/products/gu-energy-gel/ingredients-benefits_learn-the-science.) They may be easily eaten during even the most intense activities without choking or difficulty swallowing.

The instant inventor has recognized, however, that energy gels too have significant drawbacks. For example, gels are undesirably messy to consume, sticky, and tend to be environmentally unfriendly due to the common use of heavy metallic foil packaging that is discarded after each serving of the gel is consumed. In addition, the fact that each serving must be packaged individually leads to relatively large serving sizes, typically of 100 calories or more. A 100 calorie serving size enables an athlete to ingest one serving per hour to receive the recommended carbohydrate intake. This approach, however, means that the gel sits in the user's stomach for relatively long periods of time as it is digested, which can lead to stomach discomfort and is generally inefficient from an energy delivery standpoint. The present inventor has also found that many athletes complain of GI issues after using maltodextrin-based products over extended periods of time, such as during training for long distance triathlons and the like.

Gels also generates waste because it is nearly impossible to squeeze the entire serving of gel from the foil packaging, particular when attempting to do so during strenuous exercise. Still further, the foil packaging itself has been found to abrade and/or cut athletes' lips and mouths when consumed quickly during competition.

In spite of the varied and largely incongruous teachings, the instant inventor conceived that contrary to conventional wisdom, an edible solid product, composed almost entirely of simple carbohydrates, and fabricated in relatively small servings, would be an ideal solution for energy replenishment during long distance competition. He then concluded that contrary to conventional wisdom, such a product could be produced as an edible solid tablet without adding protein, fillers, or hydrophobic or PEG-containing lubricants. He further realized that contrary to conventional wisdom, his approach, despite using predominantly simple carbohydrates, would avoid the 'sugar high' concerns of the prior art as well as the aforementioned GI problems. Embodiments of the present invention address the foregoing drawbacks by providing a formula based on a high weight percentage of carbohydrate in the form of a blend of sucrose and dextrose, without protein, to provide optimal uptake for the athlete. The inventor also found that adding a proportionately small amount of maltodextrin provided additional carbohydrate while reducing the high level of sweetness provided by the sucrose and dextrose. This was found to greatly enhance athletes' ability to eat the tablet during competition without feeling the need to simultaneously drink fluids to dilute the sweetness of the sucrose and dextrose.

The inventor also recognized that lubricants commonly used for tablet fabrication, such as those that are hydrophobic and/or which have laxative effects such as PEG (polyethylene glycol) needed to be avoided, due to taste and GI issues. Embodiments of the invention addressed this issue by the use of specialized tableting equipment described hereinbelow. However, a problem still to be overcome was finding a way to bind the ingredients to provide the tablet with sufficient structural integrity to avoid crumbling during manufacture, transportation, and while being carried and ultimately eaten during competition. Athletes consuming the product while breathing heavily during strenuous exercise would not want to risk aspirating dust or small granules from a powdery, crumbling product. This binding of the ingredients also needed to be accomplished in a manner that did not adversely affect the shelf-stability of the product. For example, the inventor found that various edible oils, while capable of successfully binding the powder, tended to have relatively short shelf-stability. Another issue confronted by the inventor was the understanding that solid products tend to be too dry for athletes to eat quickly without also needing to consume a liquid.

The inventor was surprisingly able to address both the shelf-stability and dryness issues by adding a small amount of edible (e.g., citric) acid to the formula. The acid was found to provide the multiple benefits of counteracting the shelf-stability issues of the oil, of stimulating the athletes' salivary glands to facilitate eating without the need to simultaneously consume liquids, and of helping to provide proper mouth-feel, e.g., counteracting the tendency of the product to feel granular and/or chalky in the mouth.

It was also surprisingly found that the formulation, when fabricated into tablet form and packaged in bulk did not require desiccants in order to avoid moisture damage. The embodiments could therefore be configured in relatively small serving sizes, e.g., ranging from 2 to 50 grams, with several servings packed in a single relatively inexpensive desiccant-free, and optionally re-sealable, package, to enable the user to conveniently access and eat the tablets one at a time to effectively meter the carbohydrate intake and avoid having product sitting in the athletes' stomach during competition.

These embodiments efficiently provide athletes with a relatively high rate of exogenous carbohydrate oxidation during exercise, while at the same time minimizing the risk of developing problems with the gastrointestinal tract.

The inventor further recognized that non-pharmaceutical tablets are relatively difficult to produce, and even more so if the tablets are relatively large and intended to be eaten rather than simply swallowed like a pill.

Tableting presses have long been utilized to manufacture tablets by compressing powders and granules. A typical tableting press uses a cylindrical die center made of steel, and steel punches, to compress the powder under relatively high pressures, typically up to about 10 to 15 tons per square inch. One result of the compression is the production of heat. This heat builds up on the face of punches and in the die and, over a relatively short period of time, tends to cause the powder to stick to the faces of the punches and sides of the die. Once the powder begins to stick to the die and/or to the punch faces, the integrity of the tablet is compromised, since as the faces of the punches pull apart to eject the tablet, the tablet sticks to the punch faces and breaks, or is broken or damaged by the friction with the cylindrical walls of the die. Moreover, any powder remaining on the punches and/or die walls tends to add to the volume of powder within the die, to disadvantageously alter the internal pressure of the tablets. Tablets formed under excessive pressure may not be easily eaten, while tablets formed under insufficient pressure tend to break prematurely.

In order to reduce the die and face heat, and reduce the sticking on the face of the punches and the sides of the dies, it has been common practice to add powdered lubricants to the powdered tablet composition. These lubricants generally encase the powdered granules to reduce the friction on the face of the punches and the sides of the die. Commonly used lubricants include magnesium stearate and other stearates, such as sodium stearate and calcium stearate. Stearates tend to be useful as lubricants because of their relatively high viscosity and insolubility in water, which helps prevent their breakdown when used to make compressed tablets.

While the use of stearates may be satisfactory in some applications, such as in the production of pharmaceuticals, their use tends to be undesirable in tablets that are eaten, as they tend to make the tablet unpalatable.

Thus, when manufacturing an edible tablet it is important to reduce or eliminate any insoluble material in the composition. One attempt to manufacture water soluble tablets involves replacing hydrophobic lubricants, such as stearates, with water soluble lubricants such as polyethylene glycol (PEG). While the use of such water soluble lubricants tends to reduce sticking on the sides of the die, these lubricants by themselves do not adequately prevent the tablet composition from sticking to the faces of the punches. This sticking problem is particularly acute when producing relatively large tablets, in which the tablet tends to be pulled apart when the punches separate prior to the tablet's ejection from the press.

Embodiments of the present invention include a product formulation, method of manufacture, and packaging therefor, that produces an edible tablet configured to provide a source of carbohydrates that are quickly absorbed by athletes engaged in training and competitions, without the drawbacks associated with sport drinks, bars, and gels.

In particular embodiments, the inventive tablets provide a mixture of three different simple carbohydrates in 10 to 20 calorie increments which enable an athlete to effectively meter the consumption of carbohydrates. Thus, instead of consuming an hour's worth of carbohydrates at once, such as by consuming a single serving of a gel, or by consuming a sport drink and risking the associated GI issues, the athlete may quickly and easily meter his or her carbohydrate intake by eating a series of tablets over the course of an hour of competition. In this regard, the inventor has found that an intake of 100 calories of carbohydrate per hour in the form of the inventive carbohydrate tablets, is well tolerable for the GI-tract.

Figure 3:
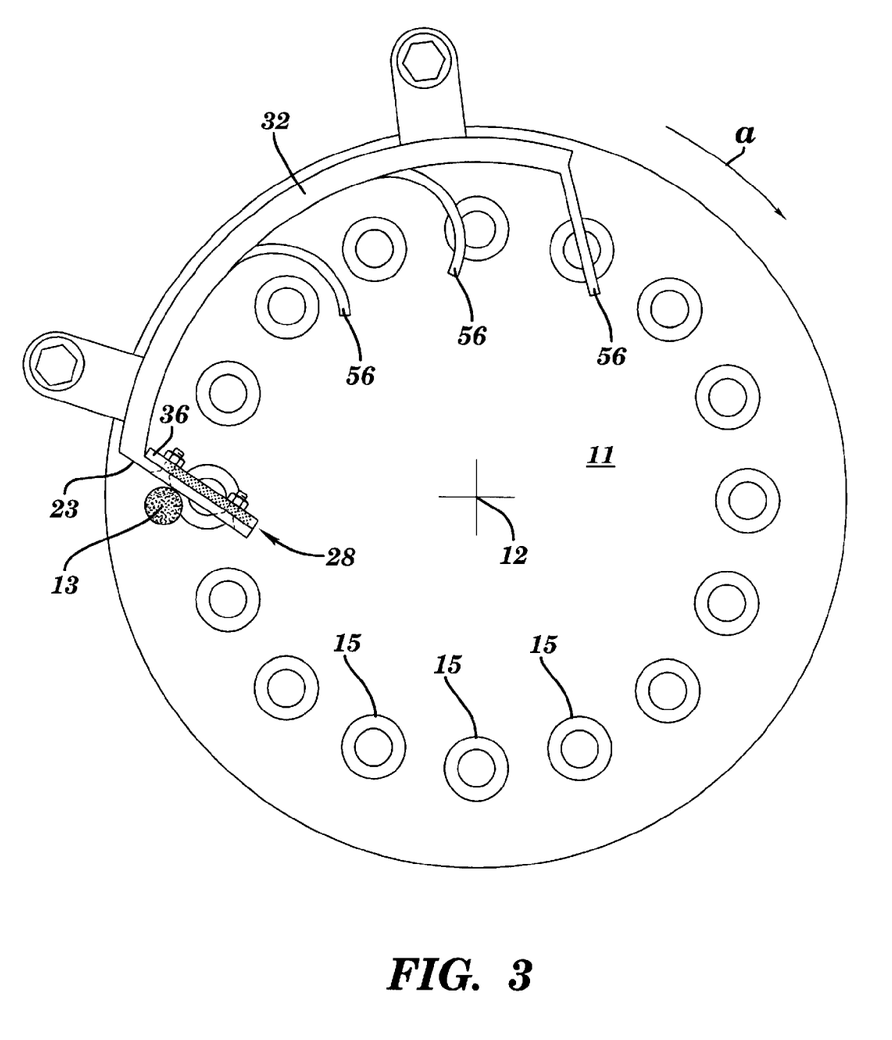
FIG. 3 is a schematic top view of a portion of the press of FIG. 1, taken generally along 3-3 of FIG. 1.

Moreover, while the subject matter of the present invention is primarily intended for athletes, it is clear that the carbohydrate tablet of the present invention can be used by anybody in need of carbohydrate supply. For example, the tablet of the present invention can be very well used as transportable food for people who do not wish to carry too heavy provisions, for example during long hiking trips. The tablet of the present invention may equally well be used by people to provide the body with carbohydrates for example before or during an examination in school or at university.

Where used in this disclosure, the term "axial" shall refer to a direction substantially parallel to rotational axis 12 (FIG. 3). The term "radial" shall refer to a direction substantially orthogonal to the axial direction. The term "coaxial", when used in connection with an element described herein, shall refer to a direction relative to the element, which extends through its geometric center and is substantially parallel to rotational axis 12 of table 11. The terms "downstream" and "upstream" respectively refer to the direction of arrow a (as the dies 15 move through filling station 20) and a direction opposite thereto.

Figure 1:
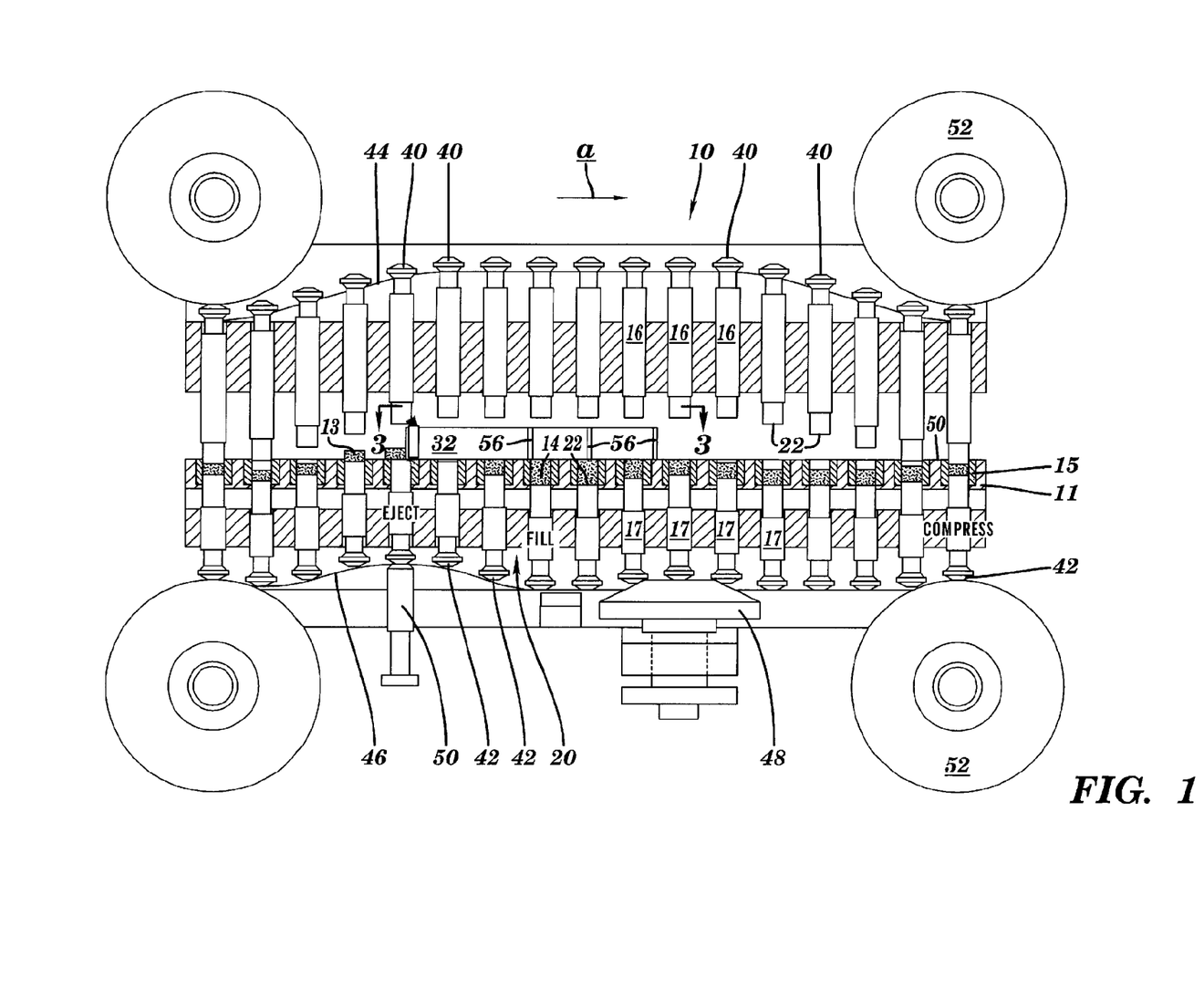
FIG. 1 is a schematic plan view, viewed from the interior, of a rotary press incorporating aspects of the present invention, used to fabricate nutritional tablets of the present invention.
Figure 2:
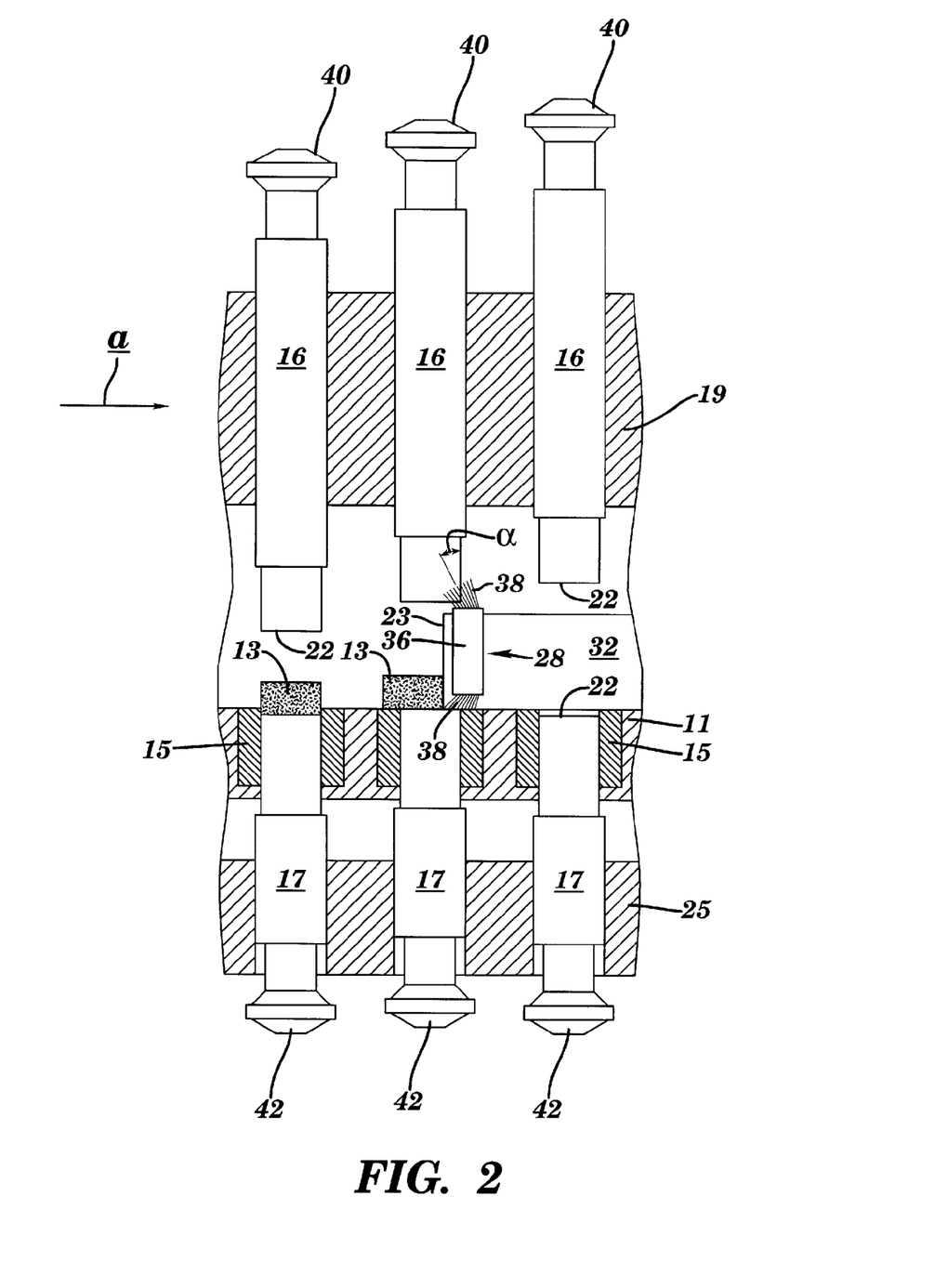
FIG. 2 is an enlarged view of a portion of the rotary press of FIG. 1.

Turning now to the Figures, a rotary press usable to produce tablets in accordance with the present invention, is shown in FIGS. 1-3 and is in many respects conventional. The press 10 has a circular die table 11 disposed for rotation in direction a about its central axis 12 (FIG. 3). A plurality of generally cylindrical dies 15 are spaced circumferentially within the table 11. Above and coaxially aligned with each die 15 is an associated upper punch 16 mounted for coaxially slidable movement into and away from a die 15 in an upper punch holder 19. The upper punch holder is in turn, arranged for rotation with the die table 11. Each of the upper punches 16 are thus sized for slidable receipt within a corresponding die 15. Similarly, below and coaxially aligned with each die 15 is an associated lower punch 17 disposed for sliding movement into and away from the die 15 in a lower punch holder 25. This lower punch holder is in turn, disposed for rotation with the die table 11 about axis 12. The proximal end of each punch 16 and 17 has a working face 22 which is adapted for engaging and compressing the powder 14 to form tablets 13 as will be discussed hereinbelow. Moreover, each of the upper punches 16 has a cam follower 40 disposed at its distal or upper end, while each of the lower punches 17 has a cam follower 42 at its distal or lower end. The cam followers 40 are supported by and slidably moveable along a stationary upper cam track 44, while the cam followers 42 are similarly supported by, and adapted for slidable movement along stationary lower cam track 46. The die table 11, dies 15, punches 16 and 17 and punch holders 19 and 25 may be fabricated from any suitable material commonly used for fabrication of dies and the like, such as metals and metal alloys, and/or composites, etc.

The lower cam track 46 is interrupted at one position by a ramp 48 the height of which may be screw-adjusted, and at another position by the head of an ejection knob 50 which may also be screw adjustable. A pair of compression rolls 52 are also associated with the upper and lower cam tracks 44 and 46, as will be discussed in greater detail hereinbelow. Since FIG. 1 is a developed view, portions of one end of the drawing, namely compression rolls 52 and one set of punches and a die 15 are duplicated in phantom at the opposite end of the drawing to help illustrate the movement of the punches 16 and 17.

The press 10 includes a hopper (not shown) for feeding powder or granules 14 to be tableted into one or more (two as shown in FIG. 1) dies 15 located at a filling station 20.

As mentioned above, in particular embodiments, powder 14 includes a sucrose and dextrose mixture of 77-95 weight percent (wt. %), and maltodextrin of 2-13 wt. % or in some embodiments, maltodextrin of 3-5 wt. %. As also mentioned above, the maltodextrin is provided in a larger wt. % than may otherwise be used in drink mixes, to help lower the sweetness of the tablet when eaten. The powder 14 may also include an edible soluble (e.g., canola) oil of 0.2-2.0 wt. %, and in some embodiments, 0.3-1.0 wt. %, to bind ingredients to avoid breathing in crumbs or dust during exercise, and to create desired mouth-feel.

An edible acid (e.g., of citric and/or ascorbic acid) of 1-4 wt. %, or in particular embodiments, 2-3 wt. %, is provided to activate salivary glands to avoid need for liquid, for eating while exercising, and to enhance shelf-stability of the oil. Flavor is provided at 0.5-3 wt. %, or in some embodiments, 0.8-1.3 wt. %, which is down from about 4% and over in drink mixes, to avoid being too flavorful for eating. It should be recognized, however, that flavor may be entirely omitted in some embodiments, without departing from the scope of the invention.

Moreover, in optional variations of the forgoing formulation, powder 14 may include rosemary at 0.2-0.4 wt. % of the soluble oil. It should also be recognized that various additional ingredients may be added in particular embodiments, as may be desired for particular applications. For example, one or more of Vitamin C, Vitamin E, Vitamin B2, Vitamin B6, and combinations thereof may be added. Other optional ingredients include minerals, electrolytes, and combinations thereof. Still further, amino acids such as one or more of L-leucine, L-valine, L-isoleucine, and combinations thereof, may be included. Other optional ingredients include one or more of aroma compounds, caffeine, ginseng, kola nut, conservatives, guarana, acidifying agents, binding agents, water, fruit, antioxidants, coloring agents, and combinations thereof.

Optionally, powder 14 may include a water soluble lubricant in particular embodiments, as will be discussed in greater detail hereinbelow. The hopper feeds the powder into the dies 15 located at the fill station 20 through a feed frame 32 superposed with the top surface 54 of the table 11. The feed frame 32 includes stationary blades 56 which extend radially across the dies for scraping excess powder or granules away from the dies 15 located within the fill station 20 as the dies rotate with table 11 relative to the stationary feed frame 32. This action will be discussed in greater detail hereinbelow with respect to the operation of the present invention.

As best shown in FIGS. 2 and 3, feed frame 32 also includes a tablet cam or ejector 23 which serves to cam the completed tablet 13 radially outward and off of table 11 as the table rotates about its access 12 in direction a. Also disposed on ejector 23 is a brush 28 which includes an elongated base 36 which, as shown in FIG. 3, is adapted to extend transversely or radially across substantially the entire diameter of each die 15 as each die rotates past the ejector 23. As also shown, brush 28 includes a pair of bristle arrays 38 extending from opposite sides of the base or block 36 to respectively engage the faces 22 of punches 16 and 17. As best shown in FIG. 2, the bristle arrays 38 are disposed to resiliently engage and clean the faces 22 of upper and lower punches 16 and 17 as the punches rotate past the brush 28. The bristles within each bristle array 38 are fabricated from any suitable material. In a preferred embodiment the bristles are fabricated from a food grade nylon (polyamide) or polypropylene. Block 36 may be fabricated from any suitable material, such as various metals (i.e. steel, stainless steel. etc.) or polymers, (i.e. acetal, nylon, polytetrafluoroethylene, etc.). The bristles are retained within base 36 in any suitable manner familiar to those skilled in the art of brush making. The diameters of the individual bristles as well as the bristle count per cross-sectional unit area are predetermined in conjunction with the elastic modulus of the particular material used, to form bristles which effectively remove any buildup of powder 14 from the punch faces 22, nominally without scoring or otherwise damaging the faces. As also shown in FIG. 2, bristle arrays 38 are preferably angled obliquely towards the incoming punches 16 and 17 (i.e. the bristles extend obliquely towards the upstream direction) to provide a relatively aggressive angle of incidence of the bristles onto faces 22. In a preferred embodiment, bristles are positioned on the block at a 10 degree angle α relative to axis 12, to provide a relatively firm and aggressive contact with the faces 22 of the punches as they rotate through the bristles. In this embodiment, as the faces of the punches rotate through the bristles, the firmness and orientation of the bristles tend to push the punches axially away from the brush, against the bias of the cam tracks 44 and 46 and force any built up powder composition to be removed from the face of the punches 16 and 17. The clean punch faces are then presented to the fill station 20, as will described in greater detail hereinbelow with respect to the operation of the present invention.

Moreover, the bristles are preferably provided with a variable length, so that relatively downstream bristles extend further from surface 50 than relatively upstream bristles as shown in FIGS. 1 and 2. Also as shown, the bristles of array 38 which extends towards lower punches 17 are preferably substantially shorter than those of the bristle array 38 adapted to engage the upper punches 16. This configuration compensates for the relatively small clearance between base 36 of the brush and the surface 50 of table 11. In one example, the bristles have a diameter within a range of from 0.003-0.030 inches (0.007-0.07 cm), with a preferred diameter within a range of approximately 0.005-0.006 inches (0.012-0.015 cm), with a bristle length within a range of about 0.3-0.5 inches (0.7-1.3 cm) i.e. about 0.5 inches (1.3 cm) on upper array 38, 0.3 inches (0.7 cm) on lower array 38.

As best shown in FIG. 1, in operation, a given die 15, having an associated upper punch 16 and a lower punch 17, is moved with table 11 to the filling station 20 (i.e. a position axially aligned with feed frame 32) where the die is filled with powder 14. As the die moves to the fill station 20, the cam follower 42 is moved down (axially away) from surface 50 of table 11 by the slope of the cam track 46 so that the lower punch 17 only slightly projects into the die and the die is thus almost entirely filled with powder 14. As table 11 continues to rotate in direction a, the cam follower 42 subsequently reaches the ramp 48 and is driven upwardly (axially towards the surface 50) to expel powder from the die. By the time the cam follower 42 is on top of the ramp 48 (i.e. at the point closest to the working surface 50) the blades 56 will have scraped away any excess powder from the surface of the die which is generally co-planar with surface 50. Thereafter, the lower punch 17 is lowered as the cam follower 42 returns to the cam track 46 and the upper punch 16 drops towards table surface 50 as the cam follower 40 slides down the inclined upper cam track 44. The upper and lower punches 16 and 17 are finally forced together by the compression rollers 52 to compress the powder 14 within the die 15 to form a tablet 13. As table 11 continues to move in direction a, the upper punch 16 is raised until it disengages both the die 15 and the tablet 13. The lower punch 17 is also raised until face 22 thereof is flush with surface 50 of the die table 11, at which stage the tablet is cammed radially outwardly by ejector 23 as best shown in FIGS. 2 and 3. The tablet is then collected by a suitable collection device (not shown). As the tablet 13 is being cammed away from table 11 by ejector 23, the faces 22 of upper and lower punches 16 and 17 are moved into engagement with the bristle arrays 38. This engagement serves to remove a majority of any buildup of powder 14 thereon as the punches and die move into the fill station 20 where the cycle of operation is repeated.

Although the present invention is shown and described in conjunction with a single stage rotary press 10, the invention may be incorporated into a conventional multi-stage press in which a plurality of tablets are produced during each revolution thereof. Moreover, the cycle of the press 10 may be modified to include various additional steps such as pre-compression of the powder 14, etc.

The present invention as shown and described herein, may be utilized with powder material 14 either with or without a lubricant. The present invention has been shown to be particularly effective in manufacturing water soluble tablets 13 without the use of conventional hydrophobic lubricants such as magnesium stearate, or lubricants having pronounced laxative effects (PEG). When fabricating such water soluble tablets 13, the present invention may be utilized either with or without lubricants. In a preferred embodiment however, any suitable water soluble lubricant may be mixed with the powder 14 prior to being fed into dies 15 as discussed hereinabove. Examples of water soluble lubricants which may be used in the present invention include crystalline maltitol, sodium benzoate, 1-leucine, starch, and sodium lauryl sulfate.

In a further variation of the subject invention, the powdered or granular material 14 may be pre-ground prior to being fed into the dies 15. For example, the powder 14 may be ground to a predetermined mesh size, preferably to a U.S. standard mesh size within a range of about 10 to 30 to provide a grit size of approximately 0.1366 to 0.0365 inches (3460 to 930 microns). This pre-grind step serves to provide the powder with a substantially homogeneous consistency to advantageously reduce the tendency of the powder to stick to either the dies or faces 22. Such pre-grinding may be utilized with either lubricated or unlubricated powder 14. In a still further embodiment, rather than being substantially cylindrical as shown, the inner surface of the dies 15 may be tapered to have a slightly frusto-conical configuration (not shown) to facilitate removal of the tablets 13 therefrom. In such an embodiment, the inner surface of dies 15 are provided with a predetermined diameter at a point substantially flush with surface 50 of die table 11, with the diameter tapering radially inwardly further from surface 50.

Embodiments of the present invention thus enable the successful production of relatively large production runs (i.e. 200,000 tablets or more) of tablets which are water soluble and non-effervescent, i.e., fabricated without the use of an effervescent material ($CO_2$ source/carbonation) and/or without hydrophobic or PEG lubricants, and thus suitable for edible tablets. Moreover, the invention enables production of relatively large tablets, within a range of about 0.5 to 1.5 inches (1.2 to 3.8 cm) in diameter, having sufficient structural integrity to prevent them from breaking inadvertently during handling, while enabling them to be easily eaten. In a particular embodiment, the tablets resist breakage forces within a range of from 8.5 to 30, e.g., 14 to 19 kilopounds (Kp) in particular embodiments, using a test well known to those in the tableting industry. Additional steps such as lubricating the tablet material with various water soluble lubricants, pre-grinding the particulate to improve homogeneity, as well as tapering the die walls and lubricating the die walls and/or punch faces may be utilized either individually or in various combinations, with the brush 28 of the present invention to effect consistent and repeatable tableting of water soluble powder material.

Because the tablets 13 are configured for use by athletes during long distance training and competition, individual foil packaging of the type commonly used for gels was undesirable, not only because of the inconvenience and environmental concerns associated with opening and discarding it while running or cycling, etc., but also because the relatively heavy gauge of this conventional foil packaging may cut athletes' mouths and/or lips during the often hurried consumption of the gel during vigorous exercise.

Figure 4A:
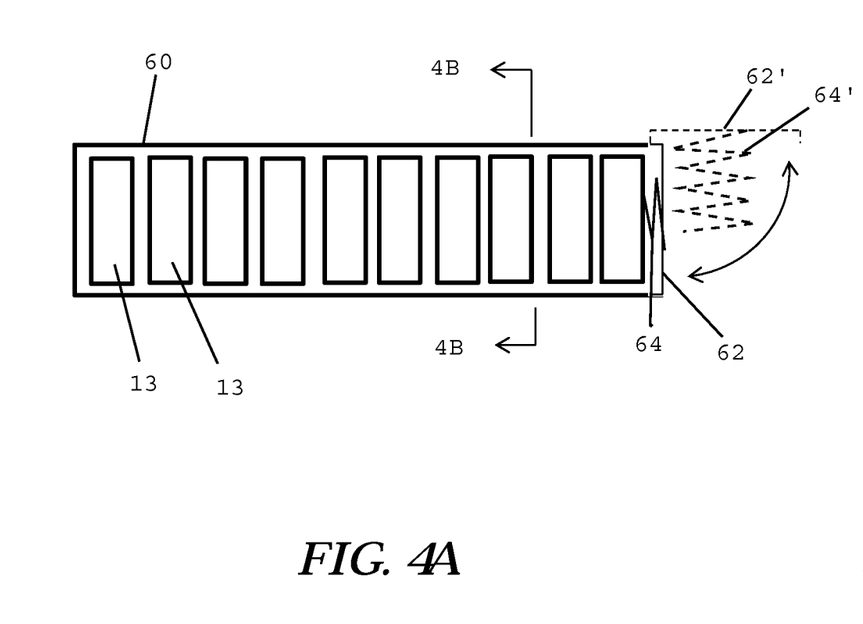
FIG. 4A is an elevational, cross-sectional view of a container holding tablets of the present invention, including a cover shown in open and closed positions.
Figure 4B:
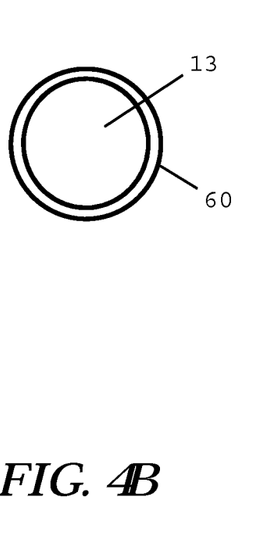
FIG. 4B is a view taken along 4B-4B of FIG. 4A.

Turning now to FIGS. 4A and 4B, in an embodiment intended to provide protection against tablet breakage, a plurality of tablets 13 may be packaged in a substantially cylindrical tube 60, fabricated from any convenient material such as paper or recyclable plastic. In particular embodiments, the package 60 is substantially rigid, e.g., injection-molded from a polymeric (plastic) material such as polypropylene or polyethylene, with a resealable, e.g., hinged, plastic cover 62, which is movable between a closed position as shown, to an open position as shown in phantom at 62'. Cover 62, 62' is configured to snap-fit onto container 60 in a conventional manner, and may include any number of tamper-resistant features, such as including a conventional break-away band that locks onto the container when the cover is first pushed onto the container after being filled with tablets.

The use of substantially rigid plastic for container 60 and cover 62 helps to provide durable protection against tablet breakage and against moisture damage to the tablets. It should be noted that the formulation of the powder 14, including its non-effervescence, and its use to form a tablet configured for being eaten as a solid rather than dissolved in liquid prior to consumption, substantially eliminates any need for use of a moisture adsorbent (e.g., silica gel or other desiccant) within or integrated with the container/cover. This feature may significantly reduce the cost of packaging relative to that of prior art effervescent tablets having integral moisture adsorbents.

As also shown, in particular embodiments, a flexible spring 64, 64' is molded into, or otherwise disposed on, the underside of cover 62, 62'. This spring helps to hold the tablets securely in place, particularly as tablets 13 are removed, to help prevent breakage while being carried by the athlete.

In a representative embodiment, the container 60 is 85 mm long×41 mm in diameter (3"×1.6"). Moreover, since formulations of the tablet powder 14, as described above, do not require the use of hydrophobic materials commonly used as pharmaceutical tablet lubricants, package 60 does not need to incorporate any adsorbent material (desiccant) of its own to trap and prevent moisture from being absorbed by the tablets. This tends to advantageously reduce the cost of the packaging relative to prior art approaches that include integral moisture adsorbents.

Alternate packaging approaches include placing several tablets 13, either in a stacked or side-by-side flat arrangement, within a relatively lightweight wrapper, such as the lightweight foil wrappers commonly used for candy bars, cereal bars, and other dry products. Again, the provision of the inventive formula in a dry tablet form factor, without the need for moisture absorbing desiccants, permits the use of these relatively inexpensive and lightweight packages. The lightweight nature of this packaging and the absence of any need to squeeze a soft product directly into the user's mouth as required by gels, substantially eliminates any tendency of the packaging to cut the users' mouths. The dry nature of the tablets 13 also avoids the messiness of gel packaging, enabling this packaging to be conveniently pocketed by the user for later disposal/recycling.

Although a unitary punch cleaner or brush 28 has been shown and described to clean the punch faces 22, one skilled in the art should recognize that a punch cleaner may be fabricated from one or a plurality of discrete components, such as resilient wipers, sponges, scrapers, brushes, etc., adapted to clean the first and/or second punch faces, without departing from the scope of the present invention.

It should be further understood that any of the features described with respect to one of the embodiments described herein may be similarly applied to any of the other embodiments described herein without departing from the scope of the present invention.

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

The following illustrative examples are intended to demonstrate certain aspects of the present invention. It is to be understood that these examples should not be construed as limiting.

EXEMPLIFICATION

Example 1

Tablet powder including sucrose and dextrose (91.7 wt. %), maltodextrin 5 wt. %, canola oil (0.3 wt. %), rosemary (0.3 wt. % of the canola oil), citric acid (2 wt. %), and flavor (1 wt. %) was mixed and fed into a conventional tablet press similar to tablet press 10 without brush 28. The powder stuck to the faces of the tablet press punches. The compositions were tableted on a Stokes Model T single station press.

Example 2

Powder formulations including the drink mix of Example 1 were prepared in five batches including 5 percent mannitol, 0.5 percent l-leucine, 1 percent l-leucine, 2 percent l-leucine, and 10 percent starch by weight, respectively. All five formulations were fed into a tablet press in the manner described in Example 1 and all five formulations resulted in sticking on the die and/or punch face surfaces.

Example 3

A tablet powder formulation was provided utilizing the tablet powder of Example 1 and fed to a Stokes Rotary DD-2 press having a brush 28 mounted onto the feed frame. The brush had bristles approximately 0.006 inches in diameter fabricated from food grade nylon. A production run of approximately 50,000 tablets was completed with minimal sticking. The size of the tablets was approximately 1⅜ inches by 0.5 inches. The tablets had a resistance to breakage forces of 18 kilopounds.

Example 4

Seven tablet compositions are provided using the drink powder of Example 1, and 1 weight percent crystalline maltitol, 3 weight percent crystalline maltitol, 1 weight percent sodium benzoate, 2 weight percent sodium benzoate, 1 weight percent l-leucine, 2 weight percent l-leucine and 10 percent starch, respectively. All of these formulations are respectively fed to a rotary tablet press substantially as described Example 4. Production runs of at least 50,000 tablets are successfully completed with minimal sticking.

Example 5

The formulations of the previous Example 4 are preground and screened with a screen having a U.S. mesh size of 20, and then tableted substantially as described in the previous Example 5. Successful production runs of at least 50,000 tablets are completed.

Having thus described the invention, what is claimed is:

1. A method for fabricating an edible energy tablet containing at least 80 weight % carbohydrates for consumption during exercise, said method comprising:
    (a) providing tablet material being free of hydrophobic and/or PEG lubricants and being free of $CO_2$ sources; the tablet material including:
        a sucrose and dextrose mixture of 77-95 wt. %;
        maltodextrin of 2-13 wt. %;
        an edible soluble oil of 0.2-2.0 wt. %;
        edible acid of 1-4 wt. %; and
        flavor 0.5-3 wt. %;
    (b) providing a tablet press including:
        at least one die circuitously moveable about the press and adapted for receiving tablet materials therein;
        a first punch and a second punch each having a working face free of external lubricants, said first and second punches being circuitously moveable with, and being adapted for operative engagement with, said at least one die;
        a punch movement device adapted to alternately move at least one of said first and second punches relatively towards and away from an other of said first and second punches to alternately compress the tablet material in said at least one die to form the tablet, and release the tablet;

a punch cleaner having resilient bristles disposable in simultaneous operative engagement with each of said working faces of said first and second punches to remove tablet material from said working faces after each of said first and second punches has released said tablet;

(c) introducing the tablet material in the form of powder or granules to the at least one die;

(d) moving the at least one of said first and second punches relatively towards the other of said first and second punches to compress the tablet material within the at least one die to form the tablet;

(e) moving the at least one of said first and second punches relatively away from the other of said first and second punches to release the tablet; and (f) automatically engaging the punch cleaner with said first and second punches to remove tablet material therefrom; and (g) sizing and shaping the die and the first and second punches wherein said tablet has a diameter in a range of about 0.5 to 1.5 inches (1.2 to 3.8 cm), a thickness within a range of about 0.25 inch to 0.7 inch (0.7 cm to 1.3 cm), and a resistance to breakage forces within a range of from 15 to 30 kilopounds; and said tablet material has a grit size in a range of about 930 to 3460 microns.

2. The method of claim 1, wherein said providing step (a) further comprises the tablet material including maltodextrin of 3-5 wt. %.

3. The method of claim 1, wherein said providing step (a) further comprises the tablet material including an edible soluble oil of 0.3-1.0 wt. %.

4. The method of claim 1, wherein said providing step (a) further comprises the tablet material including Rosemary at 0.2-0.4 wt. % of said soluble oil.

5. The method of claim 1, wherein said providing step (a) further comprises the edible acid at 2-3 wt. %.

6. The method of claim 1, wherein said providing step (a) further comprises the edible acid being citric and/or ascorbic acid.

7. The method of claim 1, wherein said providing step (a) further comprises the flavor at 0.8-1.3 wt. %.

8. The method of claim 1, further comprising disposing the tablet within a package being free of hydrophilic materials.

9. The method of claim 8, further comprising disposing the tablet within a package having a resealable cover.

10. The method of claim 1, having a resistance to breakage forces within a range of from 15 to 19 kilopounds.

11. The method of claim 1, wherein said providing step (b) further comprises providing a unitary, stationary punch cleaner having resilient bristles disposable in simultaneous operative engagement with each of said working faces of said first and second punches, said bristles extending obliquely upstream relative to the direction of movement of said die, to remove tablet material from said working faces after each of said first and second punches has released said tablet.

12. An edible energy tablet containing at least 80 weight % carbohydrates for consumption during exercise, the tablet fabricated by the process of claim 1.

13. The tablet of claim 12, wherein said providing (a) further comprises providing tablet material including a compound selected from the group consisting of minerals, electrolytes, and combinations thereof.

14. The tablet of claim 12, wherein said providing (a) further comprises providing tablet material including an amino acid selected from the group consisting of L-leucine, L-valine, L-isoleucine, and combinations thereof.

15. The tablet of claim 12, wherein said providing (a) further comprises providing tablet material including one or more compounds selected from the group consisting of aroma compounds, caffeine, ginseng, kola nut, conservatives, guarana, acidifying agents, binding agents, water, fruit, antioxidants, coloring agents, and combinations thereof.

16. The tablet of claim 12, wherein said providing (a) further comprises providing tablet material including a vitamin selected from the group consisting of Vitamin C, Vitamin E, Vitamin B2, Vitamin B6, and combinations thereof.

17. The tablet of claim 12, wherein said providing step (a) further comprises the tablet material including maltodextrin of 3-5 wt. %.

18. The tablet of claim 12, wherein said providing step (a) further comprises the tablet material including an edible soluble oil of 0.3-1.0 wt. %.

19. The tablet of claim 12, wherein said providing step (a) further comprises the tablet material including Rosemary at 0.2-0.4 wt. % of said soluble oil.

20. The tablet of claim 12, wherein said providing step (a) further comprises the edible acid at 2-3 wt. %.

21. The tablet of claim 12, wherein said providing step (a) further comprises the edible acid being citric and/or ascorbic acid.

22. The tablet of claim 12, wherein said providing step (a) further comprises the flavor at 0.8-1.3 wt. %.

23. The tablet of claim 12, disposed within a package being free of desiccant materials.

24. The tablet of claim 23, wherein the package has a resealable cover.

25. The tablet of claim 12, wherein said providing step (b) comprises providing a plurality of dies circuitously moveable about said tablet press.

26. The tablet of claim 12, wherein said providing step (b) comprises providing an ejector for removing the tablets from said at least one die.

27. The tablet of claim 25, wherein said providing step (b) further comprises providing a plurality of said first and second punches circuitously moveable with said plurality of dies.

28. The tablet of claim 12, wherein said providing step (b) further comprises the step of enabling said at least one die and said first and second punches to be rotatable around a central axis of the tablet press.

29. The tablet of claim 28, wherein said providing step (b) comprises enabling the working faces of said first and second punches to each alternately engage and release the tablet material in the die.

30. The tablet of claim 29, wherein said providing step (b) comprises adapting the punch cleaner for sliding engagement with said working faces.

31. The tablet of claim 30, wherein said punch cleaner further comprises a brush having said resilient bristles extending from a base, said bristles being adapted for said sliding engagement.

32. The tablet of claim 31, wherein said bristles are fabricated from polyamide.

33. The tablet of claim 32, wherein said bristles have a diameter within a range of about 0.003 to 0.030 inches (0.007 cm to 0.07 cm).

34. The tablet of claim 33, wherein said bristles have a diameter within a range of about 0.005 inches (0.012 cm) to 0.006 in (0.015 cm).

35. The tablet of claim 31, wherein said bristles extend from said base a length within a range of about 0.3 inch to 0.5 inch (0.7 cm to 1.3 cm).

36. The tablet of claim 31, wherein said ejector comprises a feed frame being adapted for movement relative to said at least one die, said feed frame having a surface adapted to engage and cam said tablets from said at least one die.

37. The tablet of claim 36, comprising the step of disposing said brush on said feed frame, and adapting said working face of said first punch to resiliently engage said brush as said first punch moves with said at least one die.

38. The tablet of claim 37, comprising the step of adapting said working face of said second punch to resiliently engage said brush as said second punch moves with said at least one die.

39. The tablet of claim 38, wherein said brush further comprises a plurality of arrays of bristles disposed thereon, wherein at least one of said plurality of arrays is adapted to engage said first punch and at least an other of said plurality of arrays is adapted to engage said second punch.

40. The tablet of claim 39, comprising the step of extending distal ends of bristles of at least one of said plurality of arrays obliquely relative to the direction of movement of said at least one die.

41. The tablet of claim 40, wherein said bristles of at least one of said plurality of arrays extend obliquely upstream relative to the direction of movement of said at least one die.

42. The tablet of claim 40, comprising the step of extending distal ends of bristles of at least an other of said plurality of arrays obliquely relative to the direction of movement of said at least one die.

43. The tablet of claim 42, wherein said bristles of at least another of said plurality of arrays extend obliquely upstream relative to the direction of movement of said at least one die.

44. The tablet of claim 12, wherein said providing step (a) comprises providing the tablet material with a water soluble lubricant.

45. The tablet of claim 44 wherein said water soluble lubricant is selected from the group consisting of maltitol, sodium benzoate, 1-leucine and starch.

46. The tablet of claim 12, further comprising the step of pre-grinding the tablet material prior to said introducing step (c).

47. The tablet of claim 46, comprising the step of pre-grinding said tablet material to a mesh size within a range of approximately 10 to 30.

48. The tablet of claim 12, wherein said providing step (b) comprises the step of providing the at least one die with an inner die wall of frusto-conical configuration.

49. The tablet of claim 12, having a thickness of about 0.5 inches (1.2 cm).

50. The tablet of claim 12, having a resistance to breakage forces within a range of from 15 to 19 kilopounds.

51. The tablet of claim 12, wherein said providing step (b) further comprises providing a unitary, stationary punch cleaner having resilient bristles disposable in simultaneous operative engagement with each of said working faces of said first and second punches, said bristles extending obliquely upstream relative to the direction of movement of said die, to remove tablet material from said working faces after each of said first and second punches has released said tablet.

52. The tablet of claim 12, having a serving size of 2-50 grams.

* * * * *